US008506582B2

(12) United States Patent
Kammerer et al.

(10) Patent No.: US 8,506,582 B2
(45) Date of Patent: Aug. 13, 2013

(54) TEMPLATE FOR SURGICAL MESHES

(75) Inventors: Gene W. Kammerer, East Brunswick, NJ (US); Peter Komarnycky, Lebanon, NJ (US)

(73) Assignee: Ethicon, Inc., Somerville, NJ (US)

( * ) Notice: Subject to any disclaimer, the term of this patent is extended or adjusted under 35 U.S.C. 154(b) by 1904 days.

(21) Appl. No.: 11/258,436

(22) Filed: Oct. 25, 2005

(65) Prior Publication Data
US 2007/0123915 A1 May 31, 2007

(51) Int. Cl.
*A61B 17/08* (2006.01)

(52) U.S. Cl.
USPC ............................. 606/151; 600/30; 600/37

(58) Field of Classification Search
USPC ............... 606/151; 600/29, 30, 37; 604/389, 604/390, 398; 206/363, 449, 453, 438–441
See application file for complete search history.

(56) References Cited

U.S. PATENT DOCUMENTS

| | | | | |
|---|---|---|---|---|
| 2,026,158 | A * | 12/1935 | Bennett | 604/398 |
| 6,216,353 | B1 | 4/2001 | Schenck | |
| 6,543,141 | B1 | 4/2003 | Biehl | |
| 2004/0019360 | A1 * | 1/2004 | Farnsworth et al. | 606/151 |
| 2005/0016545 | A1 | 1/2005 | Nissenkorn | |
| 2005/0288691 | A1 * | 12/2005 | Leiboff | 606/151 |

FOREIGN PATENT DOCUMENTS

| | | |
|---|---|---|
| FR | 2 864 443 A | 7/2005 |
| WO | WO 02/07648 A | 1/2002 |
| WO | WO 02/087468 A | 11/2002 |
| WO | WO 2004/045457 A1 | 6/2004 |

OTHER PUBLICATIONS

Samuelsson, E. C. et al. "Signs of genital prolapse in a Swedish population of women 20 to 59 years of age and possible related factors", Am. J. Obstet Gynecol. 180:299-305 (1999).
Olsen, A. L. et al. "Epidemiology of Surgically Managed Pelvic Organ Prolapse and Urinary Incontinence", Obstet Gynecol vol. 89, No. 4, 501-506 (1997).
Winters, J. C. et al. "Abdominal Sacral Colpopexy and Abdominal Enterocele Repair in the Management of Vaginal Vault Prolapse", Urology 55-63 (2000).
Deval, B. et al., What's new in prolapse surgery? Current Opinion in Urology 13:315-323 (2003).
Maher, C.F. et al., "Abdominal sacral colpopexy or vaginal sacrospinous colpopexy for vaginal vault prolapse: A prospective randomizer study", Am. J. Obstet Gynecol 190:20-26 (2004).
Cervigni, M., et al., "The use of synthethics in the treatment of pelvic organ prolapse. Current Opinion in Urology" 11:429-435 (2001).
Visco, A. C., et al., "Vaginal mesh erosion after abdominal sacral colpopexy", Am. J. Obstet Gynecol 184:297-302 (2001).
Boyles, S.H. et al., "Procedures for pelvic organ prolapse in the United States 1979-1997", American Journal of Obstetric Gynecology 188: 108-115 (2003).
Pang, Man-Wah, et al., "An overview of pelvic floor reconstructive surgery for pelvic organ prolapse", Journal of Paediatrics, Obstetrics and Gynaecology (2003).

* cited by examiner

*Primary Examiner* — Darwin Erezo
*Assistant Examiner* — Jing Ou

(57) ABSTRACT

Various surgical assemblies are provided, one embodiment of which includes a substantially flat template having first and second opposed sides, and having a plurality of graduated markings on said first side, and a substantially flat, flexible, surgical implant removably secured to the template and having first and second substantially flat opposed sides, and at least a first trimable portion. The surgical implant is removably coupled to the template so that the first side of the template is substantially adjacent to the first side of the surgical mesh, and so that the plurality of graduated markings are substantially adjacent to the first trimable portion of the surgical implant.

12 Claims, 4 Drawing Sheets

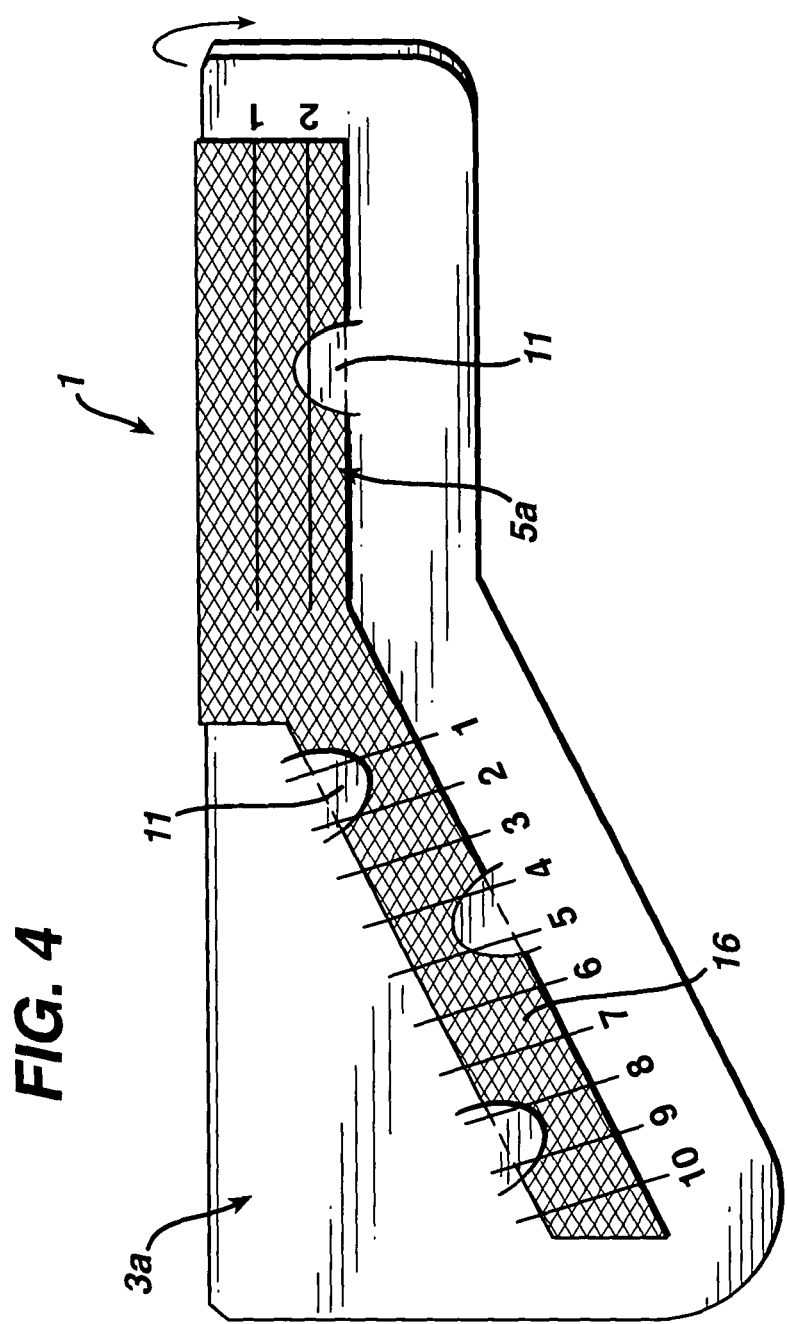

TEMPLATE FOR SURGICAL MESHES

BACKGROUND OF THE INVENTION

1. Field of the Invention

The present invention relates generally to the field of surgical implants, and more particularly to templates used in conjunction with surgical implants such as meshes to facilitate holding and accurate cutting of such implants.

2. Background Discussion

Surgical meshes are widely used in a variety of medical procedures, such as to repair hernias or various pelvic floor defects. These meshes are often supplied to surgeons in a square or rectangular shape, with the surgeons subsequently cutting or trimming the mesh according to the desired procedure, or according to the anatomy and size of the patient. More recently, some meshes have been provided in a pre-cut shape, but the surgeon is still required to trim the mesh in order to best fit the dimensions of the individual patient. This trimming and cutting of the mesh can be time consuming and difficult. Measurements taken within the patient must be transferred to measurements on the mesh before cutting or trimming can be done. Since the mesh is typically a flexible material, the mesh can be difficult to hold and manipulate during the process. This difficulty can result in less than optimal cuts or the like.

Accordingly, what is needed is an improved system and method that facilitates customization of implantable surgical meshes.

SUMMARY OF THE INVENTION

The present invention provides a surgical assembly including a substantially flat template having first and second opposed sides, and having a plurality of graduated markings on said first side, and a substantially flat, flexible, surgical implant removably secured to the template and having first and second substantially flat opposed sides, and at least a first trimable portion. The surgical implant is removably coupled to the template so that the first side of the template is substantially adjacent to the first side of the surgical mesh, and so that the plurality of graduated markings are substantially adjacent to the first trimable portion of the surgical implant.

In one embodiment, the template further includes at least one tab element, and the at least one tab element extends over a portion of the surgical implant to thereby removably secure the surgical implant to the template. In an alternate embodiment, the template further has at least one slit therein, and a peripheral portion of the surgical implant is inserted through the at least one slit to thereby removably secure the surgical implant to the template. In yet another alternate embodiment, the template further includes an implant holding means for removably securing the surgical implant thereto.

The surgical assembly may further include a film element covering the surgical implant and removably secured to the template and/or the template may include an opening therein positioned beneath the implant that facilitates removal of the implant from the template. The surgical implant may be a mesh configured for pelvic floor repair, a mesh configured for hernia repair, a mesh configured for plastic surgery, a mesh configured for breast reconstruction, a mesh configured for urinary or fecal incontinence repair, or a mesh configured for cardiovascular procedures.

In yet another embodiment, the surgical implant further includes a second trimable portion, and the template further includes a second plurality of graduated markings on said first side that are substantially adjacent to the second trimable portion.

Also provided is a surgical assembly including a substantially flat template having measuring means on a first surface thereof, a substantially flat, flexible surgical implant having a first surface positioned substantially adjacent to the first surface of the template, and having a first trimable portion, the surgical implant being removably secured to the template, and means for removably securing the surgical implant to the template. The measuring means is aligned and extends outwardly beyond a periphery of the first trimable portion.

In alternate embodiments, the means for removably securing may be a film covering the surgical implant and removably secured to the template, a slit in the template through which at least a portion of the surgical implant is passed, or a tab element projecting from the template over at least a portion of the surgical implant.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIG. 4 illustrates the assembly of FIG. 3 folded substantially along its center line, and including an alternate means by which the implant can be secured to the template.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. For example, although the present invention is primarily described herein in conjunction with surgical meshes for hernia or pelvic floor repair, it is applicable to surgical meshes or other surgical fabrics for any suitable surgical use. Suitable surgical meshes could include meshes for hernia repair, plastic surgery, breast construction, urinary or fecal incontinence, or for cardiovascular procedures to name a few.

Figure 1:
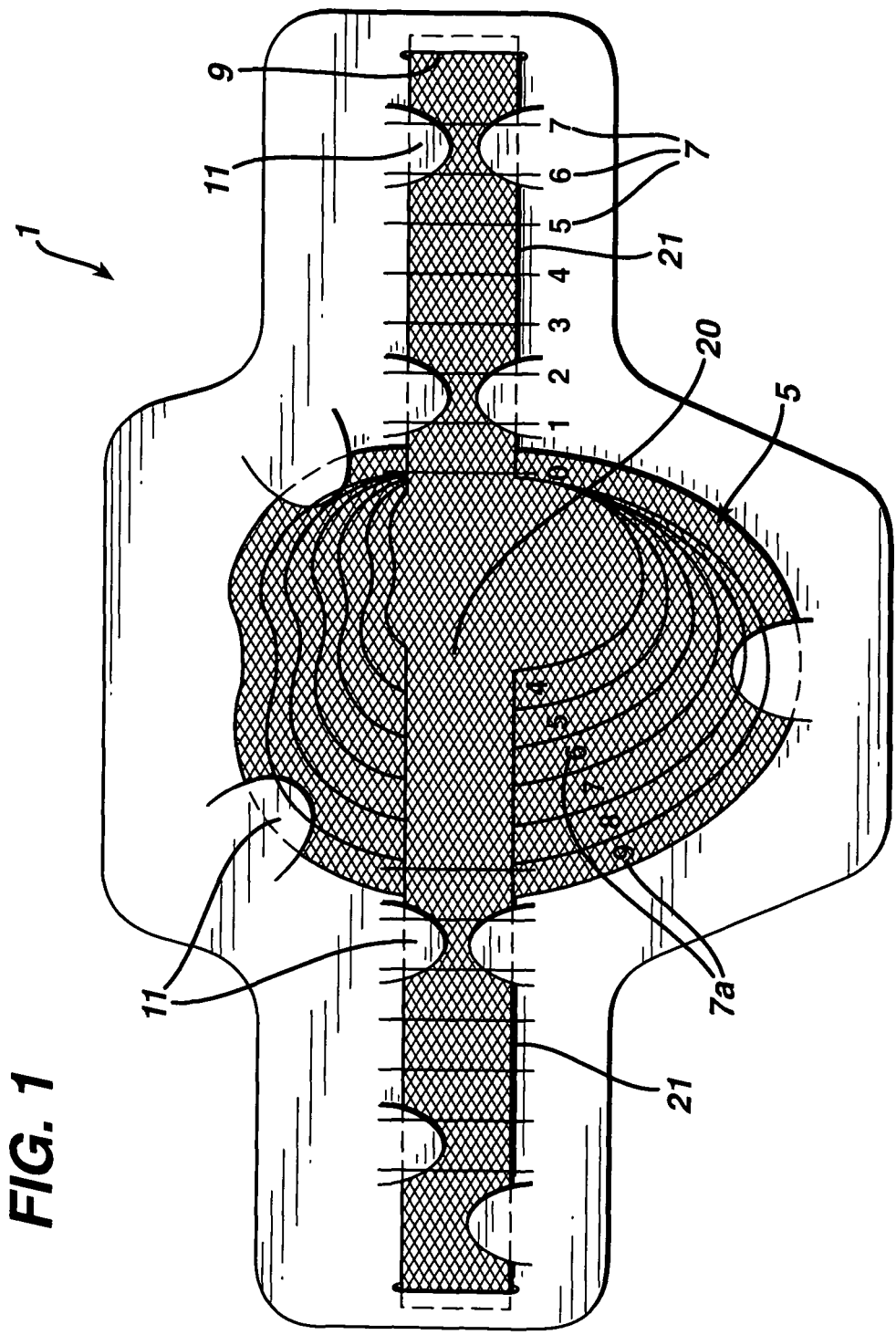
FIG. 1 illustrates a surgical assembly according to one embodiment of the present invention and including a combination surgical implant and template.

FIG. 1 illustrates one embodiment of a surgical assembly according to the present invention. The surgical assembly 1 includes a template 3 and a surgical implant 5 that is removably secured to the template. The template may be comprised of any suitable material that is sufficiently rigid to remain substantially flat when handled by a user. Any paper, cardboard, film or foam-like material can be used. The template may also be sufficiently bendable under certain circumstances to enable folding of the template/mesh assembly. For example, it may be desirable to fold the template and attached implant in half or the like, as will be described further below.

The thickness of the template may vary depending on the type of material and its stiffness. For a low density foam material, a suitable thickness is approximately 0.04 to 0.05 inches, whereas for a more dense cardboard, a suitable thickness is approximately 0.01 to 0.015 inches.

The surgical mesh 5 may be any implantable surgical mesh, or any other substantially flexible implantable fabric or material. In a preferred embodiment, the surgical mesh is comprised of a knitted polypropylene, such as those manufactured and sold by Ethicon, Inc. of Somerville, N.J. Preferably, the assembly further includes multiple size or measurement indicators or graduations 7, 7a having a purpose described more fully below. Although the illustrated graduations or graduated markings are successive lines or the like, graduated markings may include any markings that function as visual indicators of the possible different sizes. For example, the different sizes could be illustrated by different corresponding colors or shading on the template that is visible through the implant itself, or by any other suitable means.

Figure 2:
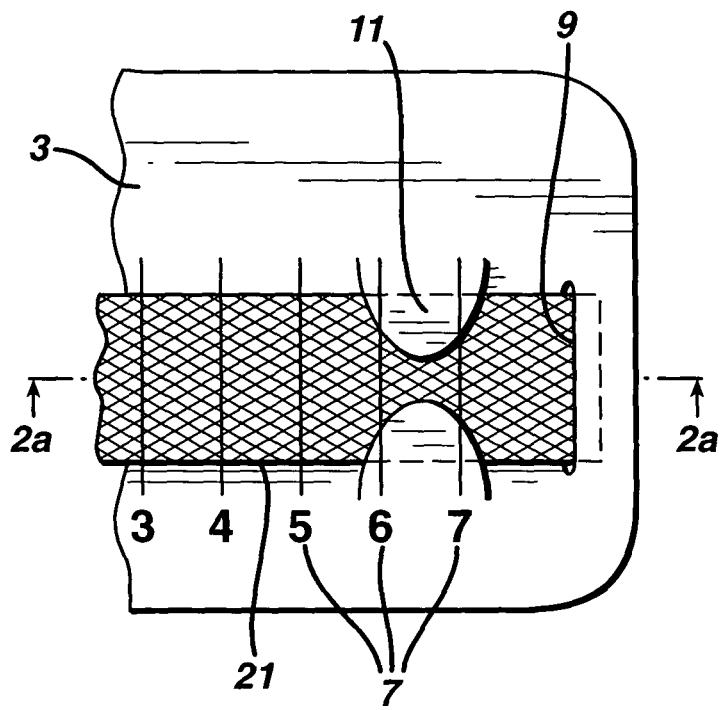
FIG. 2 illustrates one means by which the implant can be secured to the template.
Figure 2A:
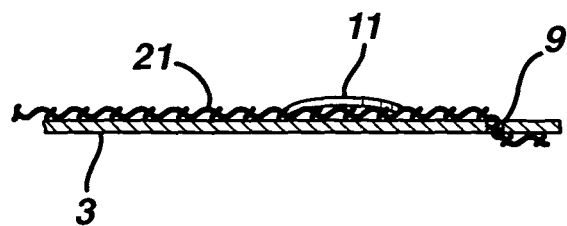
FIG. 2a is a cross-sectional view of FIG. 2.
Figure 3:
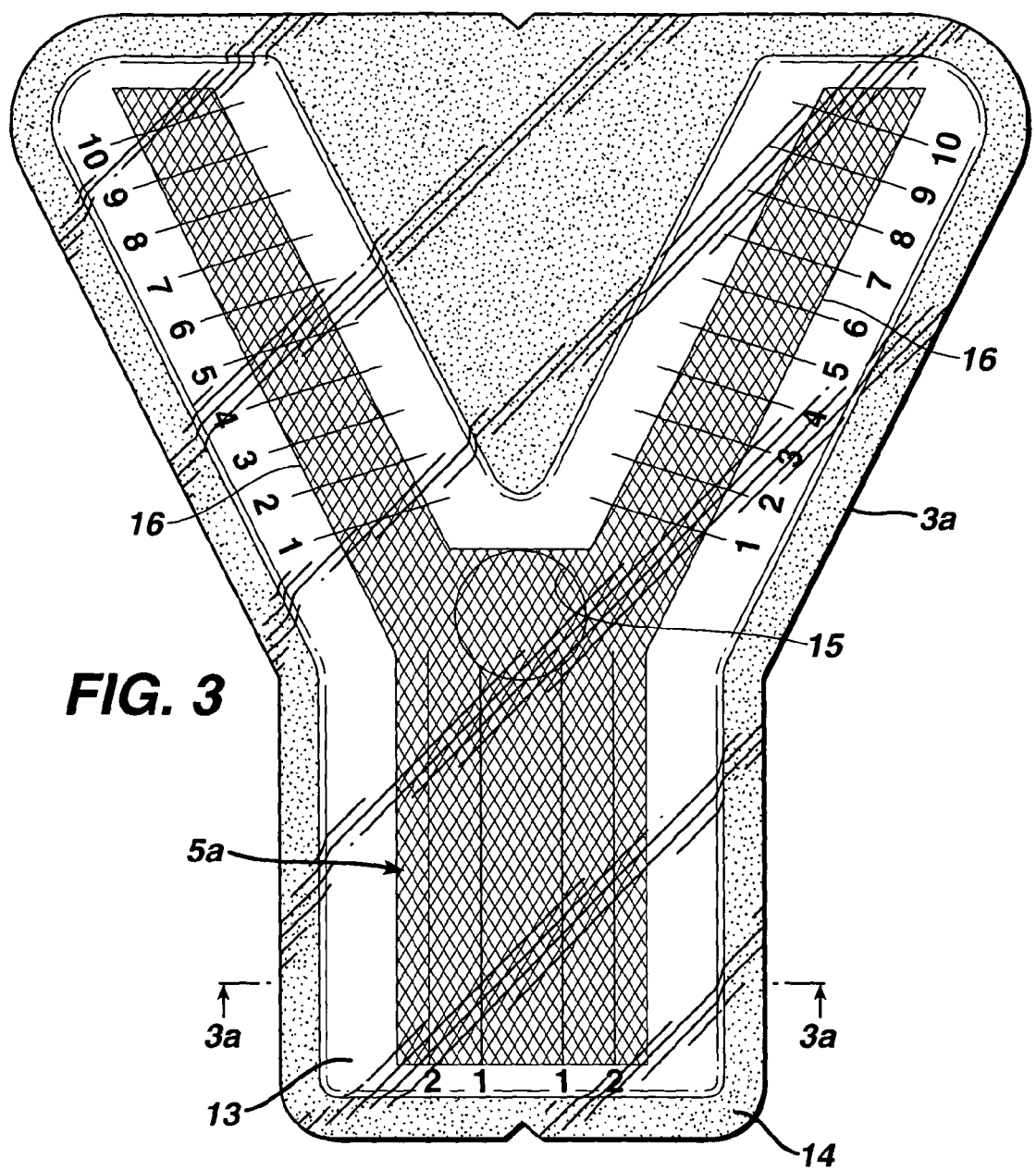
FIG. 3 illustrates an alternate embodiment of a surgical assembly including a combination surgical implant and template.
Figure 3A:
FIG. 3a is a cross-sectional view FIG. 3.

The implant 5 is removably secured in such as manner so as to substantially remain in position relative to the implant during handling and manipulation of the assembly, until a user or surgeon desires to remove the implant from the template. For example, one or more ends or areas of the implant can be inserted through a slit(s) 9 in the template as shown in FIG. 2. The implant can pass through the card a single time as shown in FIG. 2a, or multiple times to increase security. These slits may further include one or more tab-like elements 11 further projecting over the implant to provide better stability. In an alternate embodiment shown in FIG. 3, a film 13, plastic, or the like, such as polyester, is positioned over the mesh and secured to the template by any suitable means in an area 14 surrounding the implant, such as by heat sealing or with an adhesive. The film may either be peelable, or may be permanently sealed in an area surrounding the implant. In the latter case, the film "removably secures" the implant to the template, in that following cutting of the assembly as described below, a sufficient amount of the sealed area is cut off, allowing the mesh to be readily removed from beneath the film. FIG. 3a is a cross-sectional view of FIG. 3, showing the film 13 and the selected sealed area 14, with the implant 5 being captured between the film and template. A hole 15 may be cut in the template 3 to facilitate the grasping of the mesh for separation from the template. In yet another alternative, the implant can be secured to the template by a glue or other adhesive that can readily allow separation of the mesh from the template when desired. One suitable adhesive is silicone chalking.

As indicated, the present assembly facilitates the surgeon's and/or surgical room attendant's job in measuring and cutting the implant to size. The assembly and surgical implant illustrated in FIG. 1 has particular application to pelvic floor repair procedures, and more particularly to an anterior vaginal prolapse repair for a cystocele. During the anterior repair procedure a surgical mesh is implanted between the bladder and the vaginal to restore a prolapsed bladder to its normal anatomical position. In order to ensure that the implantable mesh is correctly sized for a given patient, the surgeon will measure a number of anatomical dimensions within the repair area. These dimensions will then be transferred to the mesh and the mesh will be cut to a size appropriate for the individual patient. The template and mesh of the illustrated embodiments aid the surgeon by illustrating the basic shape that best supports the weakened tissue in the particular procedure. For example, the mesh shape of FIG. 1 is designed to be placed in an anterior repair, with central body portion 20 fitting directly under the bladder and against the anterior wall of the vagina. The two lateral extension portions 21 are designed to fit into tunnels that are created on either side of the bladder.

To obtain the correct measurements and properly transfer them to the mesh, the surgeon first dissects the tissue between the bladder and vagina. Next, tunnels are created on either side of the bladder extending out to the arcus tendineous fascia pelvie and into the paravaginal space such that the inner aspect of the pubic bone can be palpated. A measurement is then taken over the pubocervical fascia from the entrance of one tunnel to the entrance of the second tunnel. This measurement is transferred to the mesh via the indicators on the template at the central body portion, starting at the 0 line located on the right side of the template at the intersection of the central body portion and the right lateral extension portion. The measurement is matched with one of the concentric rings within the central body portion. The next step is for the surgeon to measure the length of the tunnels, which is done by inserting a measurement tool into each tunnel and transferring those measurements to the mesh via the measurement indicators or graduations 7 located along the length of the right and left lateral extension portions respectively.

In this way, the present assembly facilitates the transfer of these measurements to the mesh by providing graduation markings, i.e., 7, 7a corresponding to those measurements. Thus, if the measurement obtained by the surgeon is 3 cm, the mesh can simply be cut along line 3, rather than requiring subsequent measuring along the mesh, which is time consuming and can lead to mistakes. For other surgical procedures the template 3a and mesh 5a can be arranged and preshaped so as to enhance the measurements and transfer of measurements as well. For example, the embodiment illustrated in FIG. 3 is designed for a posterior repair of a pelvic organ prolapse. The template and mesh are pre-shaped to demonstrate to the surgeon the basic shape of the implant that would best repair a rectocele or enterocele. As in the previous example, the surgeon would dissect the fascia tissue away from the vagina and, in this case, the rectum. Tunnels are then created from the posterior vaginal wall dissection to the sacrospinous ligament. Measurements are taken of the width of the rectovaginal septum area from the entrance of one tunnel to the entrance of the second tunnel, and of the length of the tunnels. The measurements are transferred to the mesh via the measurement indicators or graduations located on the template as shown in FIG. 3a. Once the template and implant have been cut to size the film cover is released from the sealed area as described above. The implant can be removed by grasping it at the center of the proximal portion which is covering the hole 15 in the card. Further, if the mesh or implant is symmetrical, it may be desirably to fold the assembly, such as in half as shown in FIG. 4, so that one cut may be made through the entire assembly 1 that accomplishes similar size cuts on both symmetrical trimable portions, i.e., 16, of an implant 5a.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A surgical assembly comprising:
   a substantially flat template having first and second opposed sides, and having a first set and a second set of a plurality of graduated markings extending respectively in first and second directions at first and second different locations on said first side; and
   a substantially flat, flexible, surgical implant removably secured to the template and having first and second substantially flat opposed sides, the implant further being adapted for implantation within a patient to treat a pelvic floor defect, urinary incontinence or fecal incontinence, and including a central body portion and at least first and second substantially straight, trimable extension portions extending outwardly therefrom and each having a width less than a width of the central body portion and a length, wherein the surgical implant is removably coupled to the template so that the first side of the template is substantially adjacent to the first side of the surgical implant, wherein the template is sufficiently rigid so as to remain substantially flat when held by a user, and is adapted to be uncoupled from the surgical implant prior to surgical implantation, and wherein when so removably coupled, the first and second sets of graduated markings are substantially aligned along and measure the length of the first and second trimable extension portions respectively.

2. The surgical assembly according to claim 1, wherein the template further comprises at least one tab element, and wherein the at least one tab element extends over a portion of the surgical implant to thereby removably secure the surgical implant to the template.

3. The surgical assembly according to claim 1, wherein the template further has at least one slit therein, and wherein a peripheral portion of the surgical implant is inserted through the at least one slit to thereby removably secure the surgical implant to the template.

4. The surgical assembly according to claim 1, wherein the template further comprises a means for removably securing the surgical implant to the template.

5. The surgical assembly according to claim 1, further comprising a film element covering the surgical implant and removably secured to the template.

6. The surgical assembly according to claim 1, wherein the template has an opening therein positioned beneath the implant that facilitates removal of the implant from the template.

7. A surgical assembly comprising:
a substantially flat template having a first surface;
a substantially flat, flexible surgical implant having a first surface positioned substantially adjacent to the first surface of the template, and having a central body portion and first and second substantially straight trimable extension portions extending outwardly therefrom and each having a width less than a width of the central body portion and a length, the surgical implant being removably secured to the template;
first and second means for measuring the length of the first and second trimable extension portions of the surgical implant on the first surface of the template; and
means for removably securing the surgical implant to the template,
wherein the first and second means for measuring are aligned along the length of the first and second trimable extension portions respectively, and wherein the template is sufficiently rigid so as to remain substantially flat when held by a user, and wherein the surgical implant is adapted to be uncoupled therefrom prior to surgical implantation.

8. The surgical assembly according to claim 7, wherein the means for removably securing is a film or other substantially translucent or transparent covering element covering the surgical implant and removably secured to the template.

9. The surgical assembly according to claim 7, wherein the means for removably securing is a slit in the template through which at least a portion of the surgical implant is passed.

10. The surgical assembly according to claim 7, wherein the means for removably securing is a tab element projecting from the template over at least a portion of the surgical implant.

11. The surgical assembly according to claim 7, wherein the surgical implant is a mesh configured for pelvic floor repair.

12. The surgical assembly according to claim 7, wherein the surgical implant is a mesh configured for hernia repair.

\* \* \* \* \*